US010893989B2

(12) United States Patent
Darrah et al.

(10) Patent No.: US 10,893,989 B2
(45) Date of Patent: Jan. 19, 2021

(54) AUTONOMOUS CRITICAL CARE SYSTEMS AND INTEGRATED COMBAT CASUALTY CARE SYSTEMS

(71) Applicant: Athena GTX, Inc., Johnston, IA (US)

(72) Inventors: Mark Darrah, Cumming, IA (US); Cesar Gradilla, Des Moines, IA (US); John Elson, San Antonio, TX (US); Gregory T. Darrah, West Des Moines, IA (US); Allen E. Brandenburg, Dripping Springs, TX (US)

(73) Assignee: Athena GTX, Inc., Johnston, IA (US)

( * ) Notice: Subject to any disclaimer, the term of this patent is extended or adjusted under 35 U.S.C. 154(b) by 131 days.

(21) Appl. No.: 16/022,955

(22) Filed: Jun. 29, 2018

(65) Prior Publication Data

US 2018/0360675 A1    Dec. 20, 2018

Related U.S. Application Data

(63) Continuation-in-part of application No. 15/274,618, filed on Sep. 23, 2016, now Pat. No. 10,361,001.
(Continued)

(51) Int. Cl.
*A61G 1/06* (2006.01)
*A61B 5/00* (2006.01)
*A61G 1/04* (2006.01)
*A61G 1/013* (2006.01)
(Continued)

(52) U.S. Cl.
CPC .............. *A61G 1/06* (2013.01); *A61B 5/0002* (2013.01); *A61B 5/0022* (2013.01); *A61B 5/6892* (2013.01); *A61G 1/013* (2013.01); *A61G 1/04* (2013.01); *A61B 5/0006* (2013.01); *A61B 5/0008* (2013.01); *A61B 5/0013* (2013.01); *A61B 5/021* (2013.01); *A61B 5/024* (2013.01); *A61B 5/0205* (2013.01); *A61B 5/02028* (2013.01); *A61B 5/02055* (2013.01);
(Continued)

(58) Field of Classification Search
None
See application file for complete search history.

(56) References Cited

U.S. PATENT DOCUMENTS 5,494,051 A * 2/1996 Schneider, Sr. .......... A61G 1/00
128/870
6,899,103 B1* 5/2005 Hood ....................... A61G 1/00
128/845
(Continued)

*Primary Examiner* — Brian T Gedeon
(74) *Attorney, Agent, or Firm* — Remenick PLLC

(57) ABSTRACT

Systems, devices, and methods for monitoring and treating a patient on route to a medical facility are disclosed. The system comprises a critical care unit; at least one patient monitoring device coupled to the critical care unit, wherein the critical care unit obtains physiological data about the patient from each patient monitoring device; at least one patient treatment device coupled to the critical care unit, wherein the critical care unit provides treatment instructions to each patient treatment device; a two way communications device coupled to the critical care unit; and a remote communications terminal in communication with the two way communications device. The critical care unit preferably sends the physiological data to the remote communications terminal and receives the treatment instructions from the remote communications terminal via the two way communications device.

31 Claims, 11 Drawing Sheets

Related U.S. Application Data

(60) Provisional application No. 62/222,617, filed on Sep. 23, 2015, provisional application No. 62/526,600, filed on Jun. 29, 2017.

(51) Int. Cl.
| | |
|---|---|
| A61B 5/024 | (2006.01) |
| A61B 5/0402 | (2006.01) |
| A61B 5/0205 | (2006.01) |
| A61B 5/1455 | (2006.01) |
| A61B 5/02 | (2006.01) |
| A61B 5/021 | (2006.01) |
| A61B 5/0476 | (2006.01) |

(52) U.S. Cl.
CPC ........... *A61B 5/0402* (2013.01); *A61B 5/0476* (2013.01); *A61B 5/14551* (2013.01); *A61B 5/14557* (2013.01); *A61B 5/6887* (2013.01); *A61B 2505/01* (2013.01); *A61G 2210/30* (2013.01)

(56) References Cited

U.S. PATENT DOCUMENTS

| | | | |
|---|---|---|---|
| 2004/0090960 A1* | 5/2004 | Holma | H04L 29/06 370/392 |
| 2009/0124868 A1* | 5/2009 | Barnett | A61N 1/3968 600/301 |
| 2012/0253847 A1* | 10/2012 | Dell'Anno | A61B 5/0022 705/3 |
| 2013/0225086 A1* | 8/2013 | Hsu | H04M 1/7253 455/41.3 |

* cited by examiner

AUTONOMOUS CRITICAL CARE SYSTEMS AND INTEGRATED COMBAT CASUALTY CARE SYSTEMS

REFERENCE TO RELATED APPLICATION

The present application is a Continuation-In-Part of U.S. application Ser. No. 15/274,618, filed Sep. 23, 2016, which claims priority to Provisional U.S. Application No. 62/222,617, filed Sep. 23, 2015, the present application also claims priority to Provisional U.S. Application No. 62/526,600, filed Jun. 29, 2017 all entitled "AUTONOMOUS CRITICAL CARE SYSTEMS AND INTEGRATED COMBAT CASUALTY CARE SYSTEMS," and all are incorporated herein in their entirety.

RIGHTS IN THE INVENTION

This invention was made with government support under Contract Number N0001414C0347, awarded by the Office Naval Research, and, accordingly, the United States Government has certain rights in this invention.

BACKGROUND

1. Field of the Invention

The invention is directed to self-contained medical care platforms. Specifically, the invention is directed to lightweight, portable self-contained medical care devices, tools and methods.

2. Background of the Invention

When transporting a patient on a stretcher, such as a NATO ("North Atlantic Treaty Organization") litter, a large metal bracket called a SMEED ("Special Medial Emergency Evacuation Device") is sometimes mounted to the side frame members of the stretcher. The SMEED extends over the patient and serves as a mounting bracket for receiving a plurality of life support devices that function independently of one another. There are several problems associated with the use of the SMEED however. One problem is that the SMEED obstructs access to the patient. Additionally, the SMEED is heavy and cumbersome to use and when attached to the stretcher adds an excessive moment arm to the attach brackets used to mount the system in a transport vehicle. Loading the SMEED with a variety of different respiratory support and monitoring devices is inefficient from the standpoint of space consumption and weight (the SMEED itself can weigh up to 22 pounds before loading any additional devices) and does not provide equal optimal access to each of those devices. Accordingly, there is a great need for a portable emergency support device that overcomes the weight, size, positioning, moment arm, and other portability disadvantages of the SMEED, allows for easy loading of various medical support devices in proximity to a subject during the course of emergency transport.

SUMMARY OF THE INVENTION

The present invention overcomes the problems and disadvantages associated with current strategies and designs and provides new tools and methods of providing portable medical support devices.

One embodiment of the invention is directed to a system for monitoring and treating a patient both at the point of injury before transport for extended times, and on route to a medical facility. The system comprise a critical care unit, at least one patient monitoring device coupled to the critical care unit, wherein the critical care unit obtains physiological data about the patient from each patient monitoring device, at least one patient treatment device coupled to the critical care unit, wherein the critical care unit provides treatment instructions to each patient treatment device, a two way, or biocommunications device coupled to the critical care unit, and a remote communications terminal in communication with the two way communications device. The critical care unit sends the physiological data to the remote communications terminal and receives the treatment instructions from the remote communications terminal via the two way communications device.

Preferably, the critical care unit further comprises a coupling device adapted to attach the system to a patient transport litter. In a preferred embodiment, the coupling device is adjustable to fit different sized liters and different support structures of various litter designs. Preferably, at least a portion of the critical care unit is adapted to be coupled under the litter and therefore under the patient. Preferably, the entirety of the critical care unit is adapted to be coupled under the litter. The critical care unit is preferably foldable into a wearable configuration. The critical care unit preferably weighs less than 30 pounds including all therapy fluids.

In a preferred embodiment, the critical care unit provides at least 90% accessibility to the patient. Preferably, the system comprising redundancies to alleviate equipment failure, to back up the system, and to run multiple similar monitors or therapeutic devices simultaneously. In a preferred embodiment, the critical care unit is adapted to interface with at least one of the medical monitors, capnography devices, IV control devices, suction devices, mechanical ventilation devices, concentrated gasses, as well as the central computing platforms, and web-based user networks and interfaces. Preferably, at least one patient monitoring device and at least one of a fluid and drug therapy device, an oxygen generating device, a ventilation device, a suction device, and an analgesia/anesthesia device will be connected to, or be integrated inside the system. The system is adapted to preferably monitor and provide treatment to multiple patients connected simultaneously while also monitor additional patients either wired to the system or wirelessly connected. The system preferably further comprises at least one visual communications device adapted to provide images of the patient to an offsite medical care giver and provide the patient with images of the offsite medical care giver. Preferably multiple visual communications devices can be connected to the platform simultaneously.

Another embodiment of the invention is directed to a portable critical care unit adapted to monitor and treat a patient en-route to a medical facility. The unit comprises at least one patient monitoring device, wherein the critical care unit obtains physiological data about the patient, at least one patient treatment device, wherein the critical care unit provides treatment instructions to each patient treatment device, a two-way communications device adapted to send physiological data, images and a voice record and receive treatment instructions, and a coupling device adapted to attach the critical care unit to a patient transport litter. Multiple systems can communicate simultaneously to the remote care provider.

Preferably, the coupling device is adjustable to fit different sized liters. In a preferred embodiment, at least a portion of the critical care unit is adapted to be coupled under the litter.

In a preferred embodiment, the entirety of the critical care unit is adapted to be coupled under the litter. Preferably, the critical care unit is foldable into a wearable backpack type of design or smaller configuration. The critical care unit preferably weighs less than 30 pounds. Preferably, critical care unit provides at least 90% accessibility to the patient.

The critical care unit preferably further comprises redundancies to alleviate equipment failure, to back-up the system, and to run multiple similar monitors or therapeutic devices simultaneously. Preferably, the critical care unit is adapted to interface with at least one of medical monitors, capnography devices, IV control devices, suction devices, mechanical ventilation devices, concentrated gasses, central computing platforms, and web-based user networks and interfaces.

Preferably, the at least one patient treatment device is at least one of a fluid and drug therapy device, an oxygen generating device, a ventilation device, a suction device, and an analgesia/anesthesia device. In a preferred embodiment the critical care unit is adapted to monitor and provide treatment to multiple patients simultaneously. Preferably, the critical care unit further comprises at least one visual communications device adapted to provide images of a patient to an offsite medical care giver and provide the patient with images of the offsite medical care giver.

Other embodiments and advantages of the invention are set forth in part in the description, which follows, and in part, may be obvious from this description, or may be learned from the practice of the invention.

DESCRIPTION OF THE DRAWING

The invention is described in greater detail by way of example only and with reference to the attached drawing, in which.

DESCRIPTION OF THE INVENTION

As embodied and broadly described herein, the disclosures herein provide detailed embodiments of the invention. However, the disclosed embodiments are merely exemplary of the invention that may be embodied in various and alternative forms. Therefore, there is no intent that specific structural and functional details should be limiting, but rather the intention is that they provide a basis for the claims and as a representative basis for teaching anyone or any group skilled in the art to variously employ the present invention and likewise interface with the invention remotely. It has surprisingly been discovered that a patient's chances of survival can be greatly improved with the use of a mobile care system that is adapted to receive data from and control a variety of medical monitoring and treatment devices. The system may be remotely controlled by a medical care giver who has access to the data and is able to send instructions to the mobile care system to control the treatment of the patient and to an onsite care provider simultaneously. For example, a doctor can access the mobile care system through the internet or secure communications links and begin to provide treatment to the patient while the patient is on route to the hospital.

Figure 1:
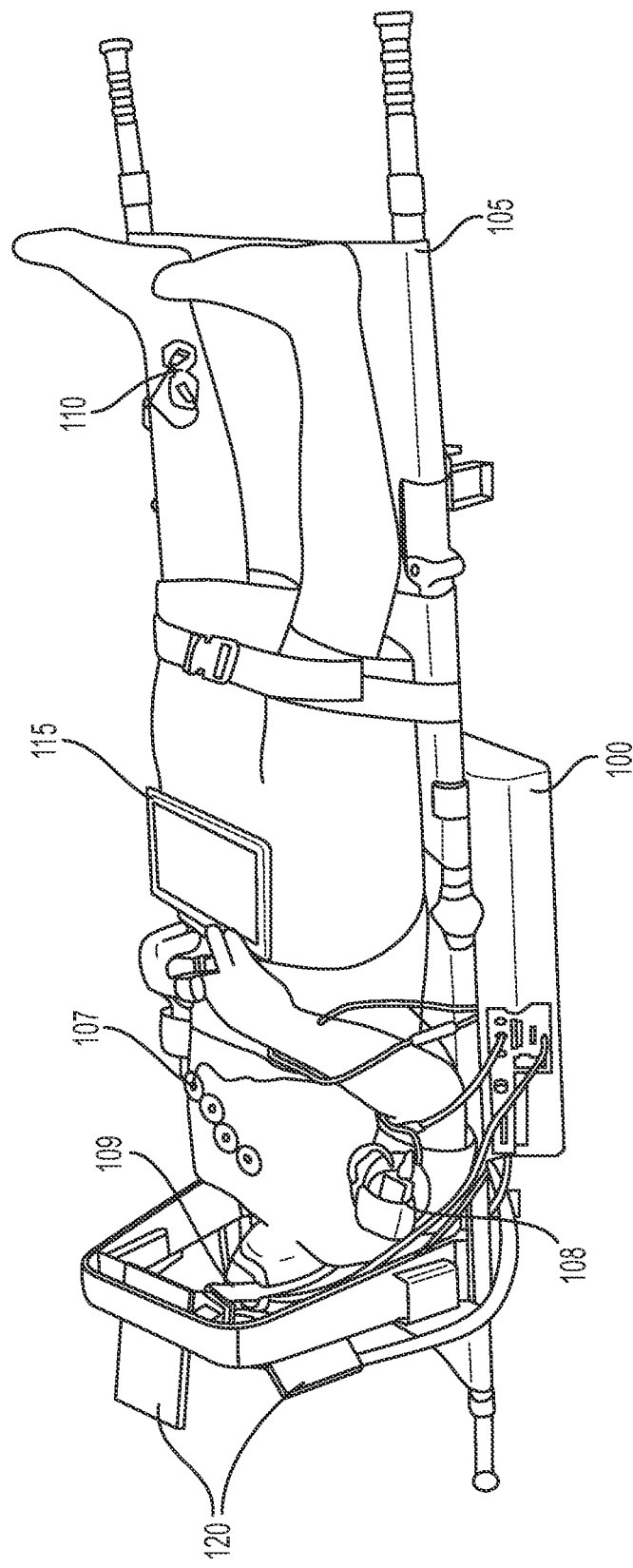
FIG. 1 depicts an embodiment of a system for monitoring and treating a patient.

FIG. 1 depicts an embodiment of an under-litter 105, medical monitoring device 100. Preferably the medical monitoring device 100 is an autonomous critical care system (ACCS). The ACCS system preferably includes computerized advanced technologies for wireless telemedicine and near real-time monitoring, ventilation technologies and sustained oxygen supply/generation, multiple channels of controllable critical care IV/IO ("intravenous/intraosseous") fluids and blood products, TCCC/PHTLS ("Tactical Combat Casualty Care/Pre-Hospital Trauma Life Support") drugs, patient and fluid warming, embedded three dimensions of Decision Support ("DS") as well as provisions for testing and evaluation. Preferably, the ACCS may include standard vital signs monitoring with body core temperature, blood pressure, pulse rate, pulse oximetry, and integration with total body impedance non-invasive cardiovascular monitoring, wireless 12 lead ECG, stroke volume, cardiac output, total body water, hemoglobin, differential pulse integrity, capnography, and cardiac power including trending of all vital signs simultaneously. Additionally, there may be data integration with ventilation, cardiac pacing, and automatic defibrillation. Preferably, advanced ONR ("Office of Naval Research") MFBS ("Multifunctional Blood Substitute") and dried plasma therapy is adapted for automatic use in the ACCS in addition with standard, or more common trauma fluids such as normalized saline (NS), Lactated Ringers (LR) and volume expanders such as Hextend® (HX). Patient cooling for advanced TBI ("Traumatic Brain Injury") or neural injuries is also possible which include r-SO2 for cerebral oxygen tension and electroencephalography (EEG). Control of the system is preferably supplied by miniature dual-redundant integrated custom computer modules, with an embedded remote physician control of patient care via a unique medical GUI ("Graphical User Interface"). Command and control is preferably provided for up to six hours of poly-trauma unmanned care which can be expanded to unlimited hours or more with manned resupply and hot swappable battery change support. The systems can be configured as a standalone single patient or multi patient system simultaneously in flight in the desired control modes offered. Software preferably automatically recognizes the peripheral devices linked wirelessly or wired and autonomously configures the display of the data streams to remote care providers as well as attending care providers via tablet and to ANDROID, Windows and iO/S platforms via connection.

Data management technology in ACCS allows the device to prioritize data connectivity via the wireless technologies used and communicate specifically to the bandwidth available and based on the criticality of the patient.

The objective of the ACCS device is to link the patient to the care provider earlier in the treatment cycle, allowing remote subject matter experts to contribute fully to improved care and elicit better outcomes. Data is preferably controlled and stored for the entire runtime of the transport allowing for subsequent analysis. Remote physicians preferably combine and summarize data feeds, as needed, and preferably can refer patients with specific needs to a subject matter expert, in order to derive existing and new medical status indices and update and integrate with improved understanding, products and therapies. Advanced predictive and anticipative models are running inside the system based on trauma state, to predict the need for life saving intervention (LSI) earlier, to adjust and change therapy and improve potential outcomes based on patient vitals and ETA.

Preferably, the ACCS 100 can be coupled to the underside of a litter 105 and provides at least 90% accessibility to the patient. Preferably, the ACCS 100 has adjustable couplings adapted to fit different sized litters. The ACCS is preferably less than 30 pounds and more preferably less than 15 pounds without significantly changing the center of gravity of the patient on a stretcher. Preferably, the ACCS is adapted to run on rechargeable batteries for up to 6, up to 8, or preferably up to 12 hours without recharging. Preferably, the batteries can be hot-swapped or changed while the ACCS is running without interrupting any medical or communications function. Additionally, the ACCS may be adapted to plug into conventional wall outlets (AC) and run off of direct current 24 VDC sources. Additionally, the ACCS can be charged and run through connected photovoltaic power as well when available. Preferably, the ACCS is adapted to withstand shock, vibration, moisture and dust. For example, the ACCS may be water and wind proof, hermetically sealed, or otherwise impervious to the elements and use in the environment.

As shown in FIG. 1, various medical monitoring and therapeutic devices (106-110) are preferably simultaneously controlled by the ACCS 100. Preferably ACCS 100 has redundancies to allow for equipment failure, backup, and running multiple similar monitors or therapeutic devices (e.g. providing multiple IV lines simultaneously). ACCS 100 may be in data communication with an external input device (for example PC, tablet 115, or a smartphone). The external input device may allow an onsite care giver to input information about procedures or medications already given to the patient and track status of remaining connected fluids and medications. Preferably, the ACCS 100 has one or more interface points, unified controls and integrated displays.

Figure 2:
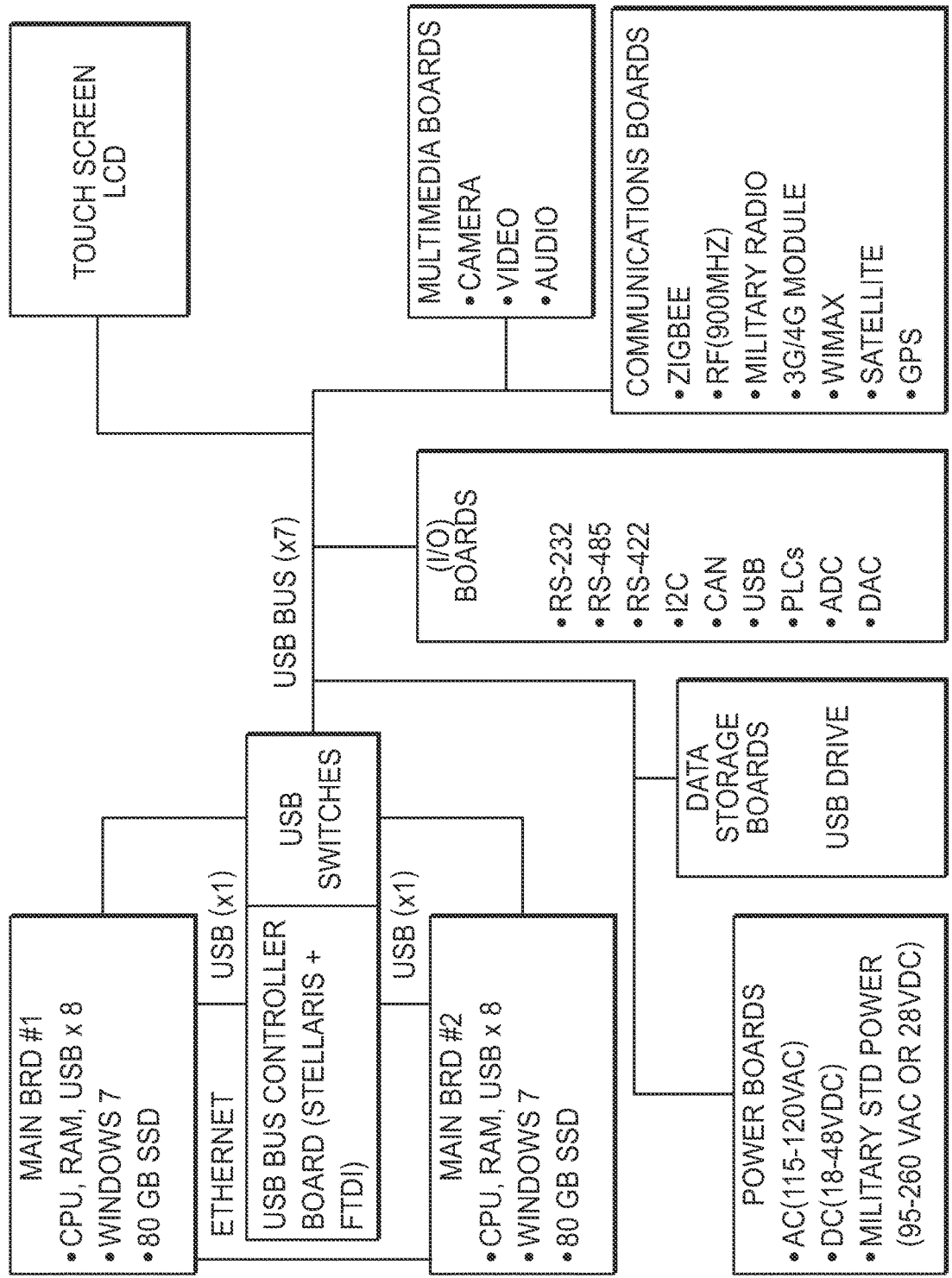
FIG. 2 depicts a schematic of an embodiment of the components of the system in FIG. 1.
Figure 3:
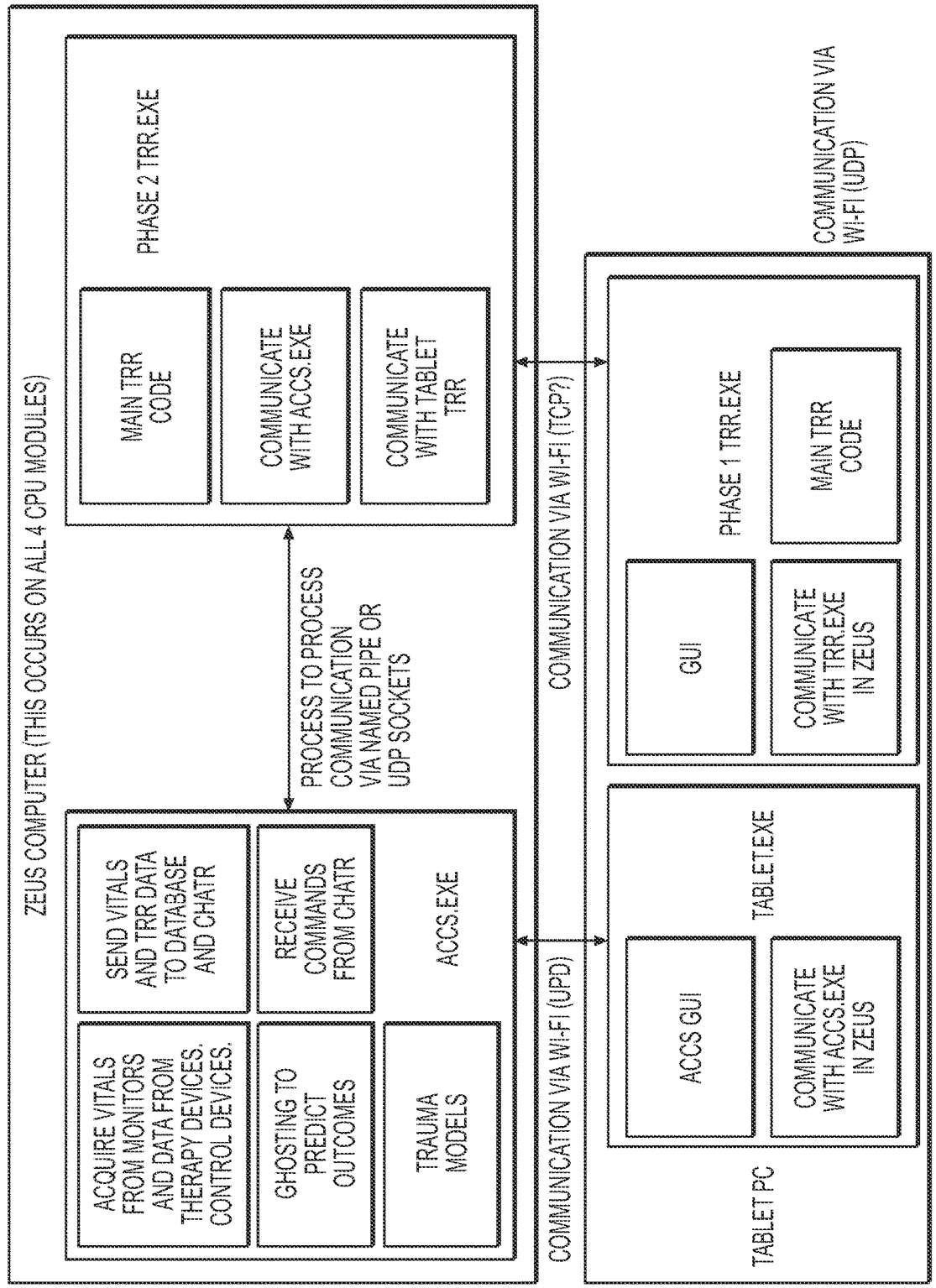
FIG. 3 depicts a schematic of an embodiment of the software used in the system in FIG. 1.

FIG. 2 depicts a schematic of an embodiment of internal computer system of the ACCS, while FIG. 3 depicts a schematic of an embodiment of associated software. Preferably, the ACCS system communicates with multiple wireless and wired hardware devices. Such devices may include, but are not limited to medical monitors (e.g. a defibrillator, or an ECG), capnography devices, IV control devices, suction devices, mechanical ventilation devices, concentrated gasses, central computing platforms, and web-based user networks and interfaces. Preferably, the main computer system comprises a CPU ("Computer Processing Unit"), memory (e.g. RAM and/or Flash), wireless (e.g. Wi-Fi and/or Bluetooth) and wired communication protocols. Preferably, the main computer system controls subservient systems and all systems share data to allow duplicate control with minimal delay.

Preferably, main processor boards will communicate with ASBs ("Analog Sensor Boards") or SCBs ("Sensor and Control Boards") via SPI ("Serial Peripheral Interface") that is not susceptible to lost bits, noise, and missing slave devices and will communicate via Ethernet allowing dual redundancy in case of a failure. The design preferably has at least two CPU boards in a master/slave design. Errors, thread, and board status will preferably be logged and available to transmit. Preferably, each USB port on the communications board will be separate and will not affect other ports if it fails. Data is preferably stored using a proprietary file format which is not prone to errors during power loss. The system may have multiple threads of execution running different algorithms in parallel reporting to a master thread. The system preferably allows complex DS to be engaged and distributed DS for different patient responses. The system preferably balances redundancy, failure modes, reliability and maintainability.

Preferably, the system has unlimited and redundant monitor capability. For example, in FIG. 1 there are three screens 120 positioned on a support around the patient that allows the patient to interact with an off-site medical care provider. For example, the off-site medical care provider may be able to view the patient to assess the patient's condition through cameras. The baseline consists of display boards with HDMI and VGA will connect to a remote monitor. The system is preferably populated with boards that are hot swappable or changed out on sensor and PC modules. Data is preferably stored using a common/standard file format such as FAT or FAT32 with multiple redundant storage devices, including a removable data storage device. Preferably, power boards enable the device to be powered by various power sources available to military personnel. GPS board preferably runs diagnostic location and determines positioning. The system preferably has multiple threads of execution running different algorithms in parallel reporting to a master thread. The system preferably allows complex DS to be engaged and distributed DS for different patient responses. Preferably, the system balances redundancy, failure modes, reliability and maintainability. Individual sensor and control boards (SCBs) are integrated into the system and operate independently. Complex patient information is asynchronously collected and processed by each of these SCBs. The main processing board communicates with the SCBs using a combination of high-speed SPI and UART ("Universal Asynchronous Receiver/Transmitter"). Various framing and checksum protocols are employed to guarantee data integrity during communications. The main processing board and SCBs maintain a "master-slave" relationship, whereby the SCBs operate under the direction of the main processing board. However, where appropriate, the SCBs can detect if they are no longer being properly controlled and respond by disengaging or maintaining state. In another embodiment, the system is preferably designed with highly efficient ASB communication via SPI. The device is preferably the SPI master and any ASBs are the SPI slaves. Each ASB preferably has algorithms built-in to allow safe operation in case of a communications failures. The ASB may be able to automatically determine that it is no longer being properly controlled by the application.

Preferably, the system provides a dynamic bio-control system (DBCS) concept. Automation is control by logic and coded based on therapy decisions derived from vital signs and has a tiered layer of application. The DBCS, on the other hand is an algorithm that creates an overall medical physiological status of the patient based on the ongoing dynamic vitals data feed (what it knows) and predictive models of outcomes (what that means) based on current therapy (what it is doing). The DBCS, based on the current state and what that means and what is being done, predicts with a simulated patient the outcomes if nothing else changes.

For example, if the patient, suffering from hypovolemic shock, leg loss and potential femur and pelvic fracture due to an IED with an EBL of about 30-35% has been stabilized and resuscitated with a combination of a bolus of warmed normal saline and recommended Hextend and tourniquets are in place. Vitals are improved and appear serious (Class 2 or 3 shock) but it is determined to be fine for now. Pain medication is applied. The ACCS knows that after 30 to 60 minutes, only about 25 to 33% of the volume expander remains in the circulation, so it focuses on rate of change of the vitals or trends as the corpsman renders care to another patient; especially at that time where the system expects the infusate is no longer going to be in the circulation. Picking up an increase in ventilation rate over time, slowly increasing heart rate, change in etCo2 cardiac output, and an insidious but progressive change in peripheral resistance from NiCas. The DBCS knows this is not hyperventilation from ACCS, or the sedative, so it predicts a compensatory reaction to patient deterioration is continuing suggesting a slow decline. Determining the rate of decline is an issue for CASEVAC, it alarms the corpsman what it suggests is a further insult or slow bleed internally and suggests an LSI before transport. As manifested herein that decline is a predictive warning that decompensation is likely and when that decompensation may occur without further intervention. Otherwise, the probably of patient decompensation is about 90%.

The data from any connected system components is preferably captured, stored, and displayed (both patient and system information) with preferably at least 99% accuracy. Preferably, the system provides for smart closed-loop-control maintenance of body temperature at +/−1 degree F. Preferably external physiological and hemodynamic monitoring system components: monitor, record and display heart rate (derived from ECG); have 3-12 lead ECG monitoring capability; have arrhythmia detection and alarm capability; capture and record respiratory rate, pulse-oximetry, and non-invasive cardiac output, total peripheral resistance, stroke volume; have multiple channels for intravascular catheters; have clinical parameters and waveforms that are visualized with at least 99% accuracy during movement; and have wireless patient monitoring capability to include SPO2. Preferably fluid and drug therapy external components: are decision-assist and closed-loop control capable; record (date and timestamp) patient measurements and interventions, and cumulative total fluid received (infused and net volumes); have decision-assist and closed-loop control algorithms control rate and volume of multiple fluids (crystalloids, colloids, blood/blood products); have fluid warming to approximately 40° F. capability; be rapid fluid infuser capable (e.g. 6 L/hr) with free-flow protection and vented bubble detection/removal; have industry standard alarms (audio and visual), including low battery alarm; provide a library of medications of commonly used drugs to treat trauma patients (e.g. epinephrine, phenylephrine, dopamine, vasopressin, paralytics, etc.), and a system to allow drug calculations.

Preferably, the ACCS includes an oxygen generating system that: provides at least 6 L/min of 93% United States Pharmacopeia (USP) oxygen (+/−) 5%; provides inspired oxygen (FiO2) range of 21% to 100%; controls low flow oxygen source to maintain stable FiO2. Preferably, the ACCS includes a ventilation system that: has a filter system for ventilation that is 100% CBRN effective; has decision-assist and closed-loop algorithms for delivery of FiO2 (21-100%) and positive end-expiratory pressure (PEEP) (0-25+/−1 cm H2O); has a flow capable ventilator (100 L/min at 40 cm H2O); controls low flow oxygen source to maintain stable FiO2+/−5% and an alarm; has pressure- and volume-controlled ventilation modes for pediatric and adults; accepts oxygen input pressure of about 35-70 psi; displays and monitors inspired oxygen concentration (FiO2) and end tidal CO2; provides humidified oxygen (100% saturation); allows administration of aerosolized medications; has programmable standard of care alarms, including low pressure, high pressure, apnea, low source gas pressure, power supply low, low minute ventilation, high respiratory rate; has decision-assist algorithms for each alarm condition; automatically restarts after unexpected loss of power with user approved settings before reinitiating; creates exportable records of ventilator performance; displays operational time remaining for battery life; and has time stamp, capture and playback capability for waveforms and significant events.

Preferably there is a suction system that: is capable of suctioning with variable digital control and intermittent and constant suction capable of high/low endotracheal tube, gastric, and chest tube; has controlled suction capability (10-300 mm Hg); and has pop-off valves. That suction system preferably has a drain function that will not compromise the ability of the system to continuously operate. Preferably, there is an Analgesia/Anesthesia system that has standard of care and total intravenous anesthesia (TIVA) capability and is BIS monitoring capable. Preferably, the external components have manuals, simulation and training software to familiarize medical personnel with operation and maintenance of each system.

The system preferably has wireless capability that provides for physician monitoring of patient status and a system override capability from a remote medical treatment facility and has wireless patient monitoring capability. Preferably, the system is accessible over the internet from remote locations. For example, the system may use military radios, cellular networks, satellite networks, or Wi-Fi networks to communicate with the internet. Due to the dynamically changing and often limiting bandwidth available for medical information, including but not limited to medical vital signs data flow, a hierarchy of data flow may be implemented in the system. Preferably, the relative importance of data obtained from one or more casualties is determined. The system then preferably transmits the information or a summary of the information that is most important to remote care provider(s) without compromising clarity of medical state of those casualties. The pathway for that communications link may vary on operational location, presence or absence of hardware or bandwidth based on priority of data. In parallel the summary status of the patient may change and the priority of transmitting said data changes with that summary state. As the number of casualties increases the volume of data sent may likely also increase linearly. Any system that compiles medical data and seeks to transmit said data to a remote subject matter medical expert may use the throttling technique.

For example, the hierarchical priority of data may be as follows:

1. Patient ID (character string) and Summary Status (Single Character) and Time of Last Transmission (LT)—in minutes (three characters). This data is estimated to be less than 0.5 KB. A summary state preferably drives frequency of transmission (The summary state uses current vitals and trend changes).
2. Base FDA data—called Base "5" Core Vitals (HR, SpO2, RR, NIBP and etCO2). For example, HR may be three characters, SpO2 may be three characters, RR may be two characters, NIBP may be three characters/three characters, and etCO2 may be two characters. This transmission is estimated to be less than 1 KB each. Each patient's baseline is preferably separated by summary state, and triggered by summary state change. For example, a change in state may trigger a new transmission or 0-1 state transmits every 30 seconds, 2 state transmits every 15 seconds, 3 state transmits every 10 seconds, and 4-5 states transmit every 5 seconds.
3. Vital Signs and each parameter's trend direction. This data is estimated to be less than 0.5 KB. The transmission may be initiated on State change and continual on any state 2 or above 4. TCCC card (MOI, Drugs, Therapy)—captures field care. This data is preferably transmitted one time and may buffer. The data is estimated to be 1-2 MB.
5. ACCS System Therapy Settings (Vent, Fluids, Suction, Drugs). This data is preferably transmitted one time upon the system capturing the data and then retransmitted only if there is a change. This data is estimated to be 10 KB. Any changes sent back are estimated to be another 10-20 KB.
6. Waveforms. This data is sent on request of an on-site or remote care provider or in states 4-5 or higher. The data is estimated to be about 1000 KB.
7. Advanced Data (and other Devices). This data is estimated to be be 100 KB to 5 MB with waveforms.

While a certain hierarchy is described, the transmissions can occur in any order. Furthermore, other transmissions may be included and/or listed transmissions may be excluded. The system may be able to reorder the hierarchy based on patient data or an off-site practitioner may be able to reorder the hierarchy. Preferably, the system breaks the information into packets of data for transmission.

Preferably, the system has manually adjustable audible and visual alarms over an intensity range of 0-100% with 99% effectiveness and accuracy while operating. The system preferably uses industry standard data storage and data transfer technology to capture, store, and display both patient and system information at a minimum of 72 hours. The system preferably has an open architecture to log and store patient clinical parameters and waveforms at a minimum of 72 hours, provide for data transfer between the device and a remote medical treatment facility, and has simulation and training software to familiarize medical personnel with operation and maintenance of device.

Figure 4:
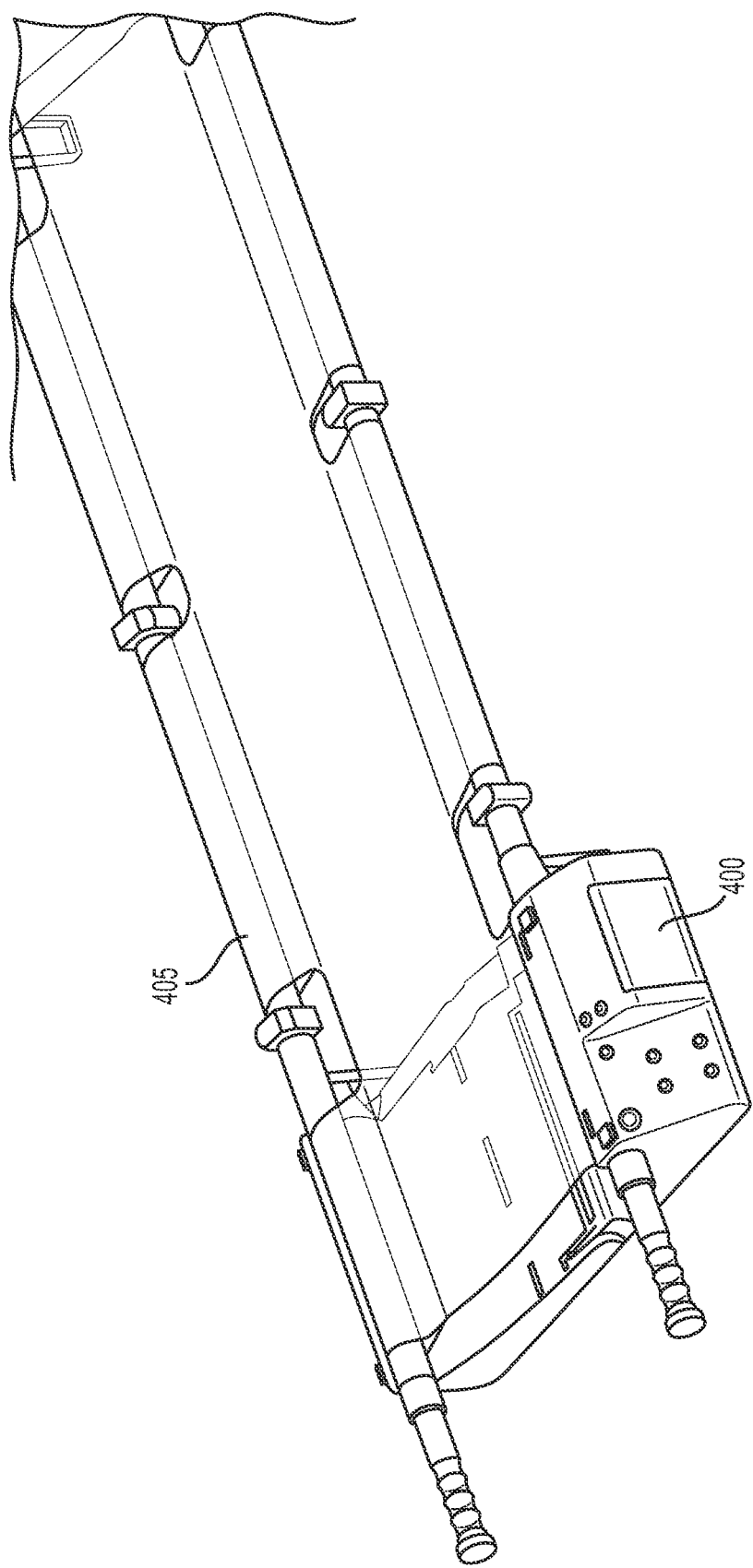
FIGS. 4 and 5 depict another embodiment of a system for monitoring and treating a patient in two configurations.
Figure 5:
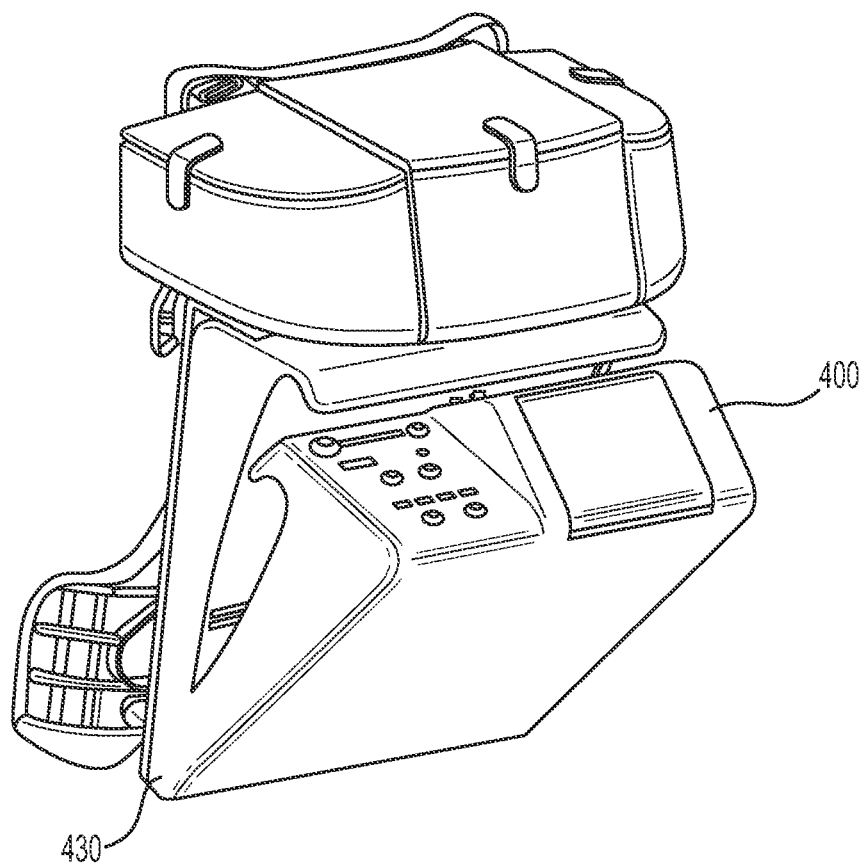

FIG. 4 depicts an embodiment of an Integrated Combat Casualty Care System ("ICCCS") 400 coupled to a litter 405. FIG. 5 depicts the ICCCS 400 folded into a wearable configuration (i.e. the backpack in FIG. 5). Preferably, the ICCCS is similar to the ACCS, however the ICCCS is lighter than the ACCS and has a quick release hinge 430 that allows the ICCCS to fold into a wearable configuration. The ICCCS system is preferably reduced in weight and bulk from the ACCS to a 10-12 pound backpack option. ICCCS is preferably a modular, highly mobile system consisting of two processing modules, two power modules, and one peripheral module. The two processing modules are preferably configured as a Dual Modular Redundant (DMR) system in a master/slave configuration. The peripheral module preferably consists of several independent channels with interface to a miniature high-performance ventilator, two or more channels of fluids via PSID which are user-controlled, with controllable fluid warming on each channel, two or four independent channels of controllable suction with fluid storage and state of the art monitoring. ICCCS preferably provides single or multi-patient control access via ANDROID or tablet with electronic TCCC. The device is preferably fielded with abilities to link wirelessly or wired and can communicate with wireless battlefield communications systems when cleared and available. The ICCCS device preferably integrates oxygen generation but can alternatively integrate with other oxygen delivery mechanisms.

Figure 6:
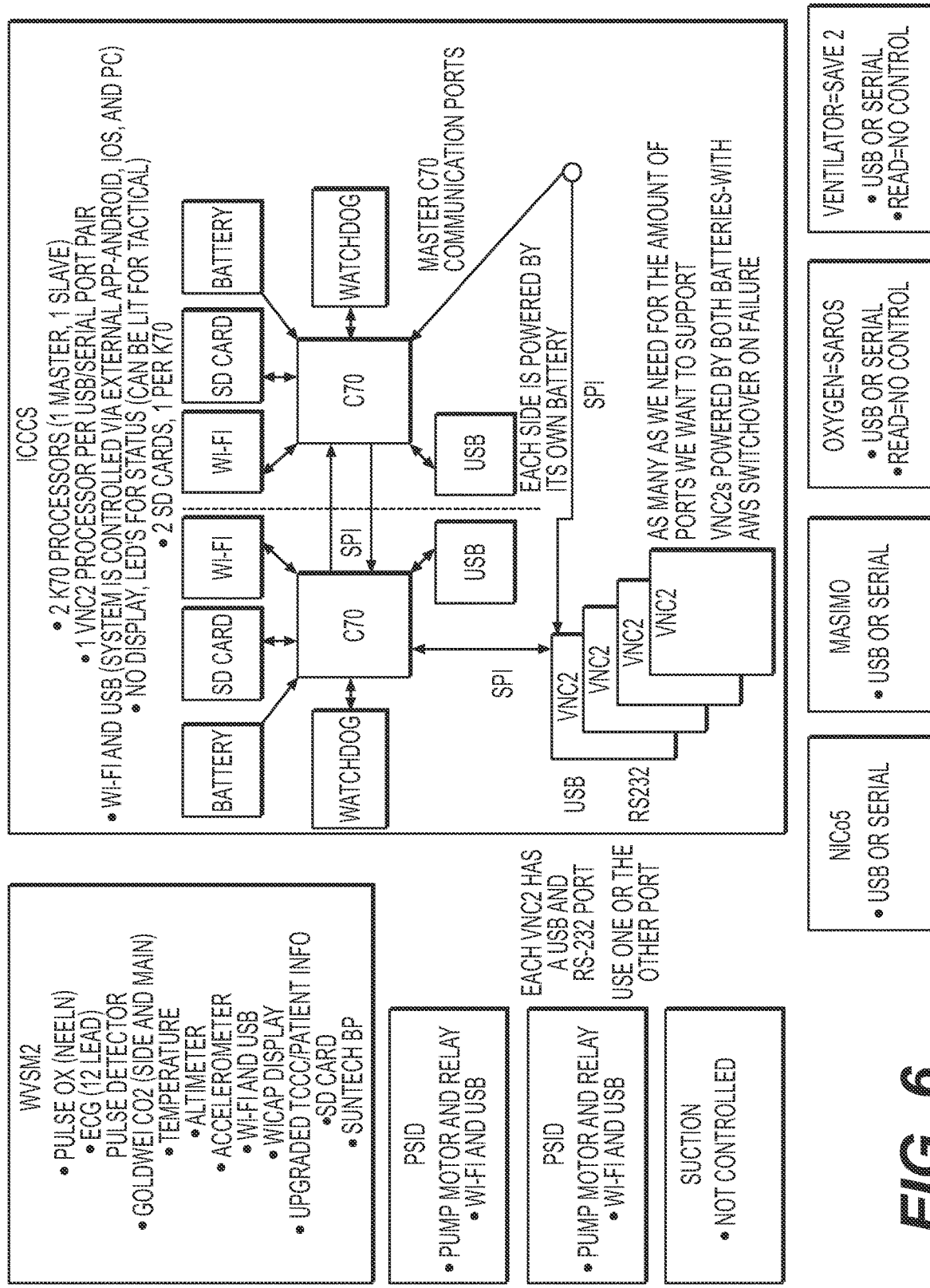
FIG. 6 depicts a schematic of an embodiment of the components of the system in FIGS. 4 and 5.

The ICCCS is preferably a modular, wirelessly enabled, complete critical care solution for use with manned and unmanned medical transport and evacuation operations. It exercises the highest level of automation and decision assistance possible for such systems. The core functionality for the ICCCS is preferably provided with multiple connected hardware devices, software and user-interfaces. FIG. 6 depicts an embodiment of the ICCCS system layout.

Figure 9:
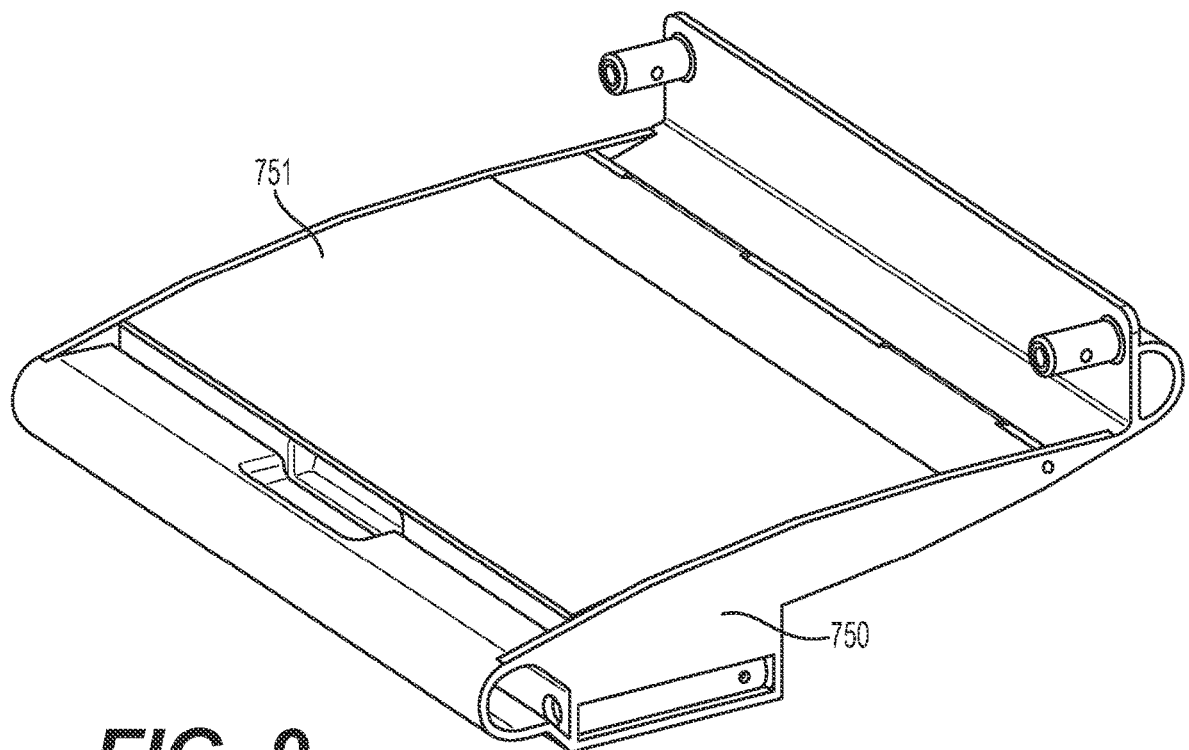
Figure 10:
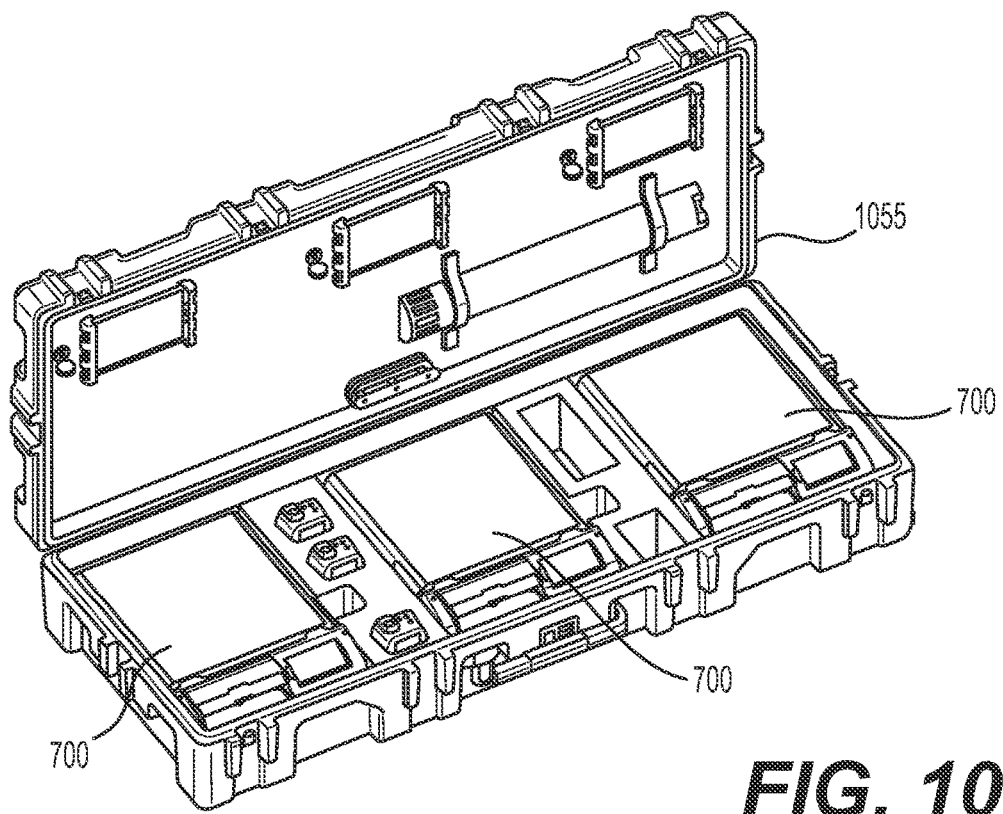
Figure 11:
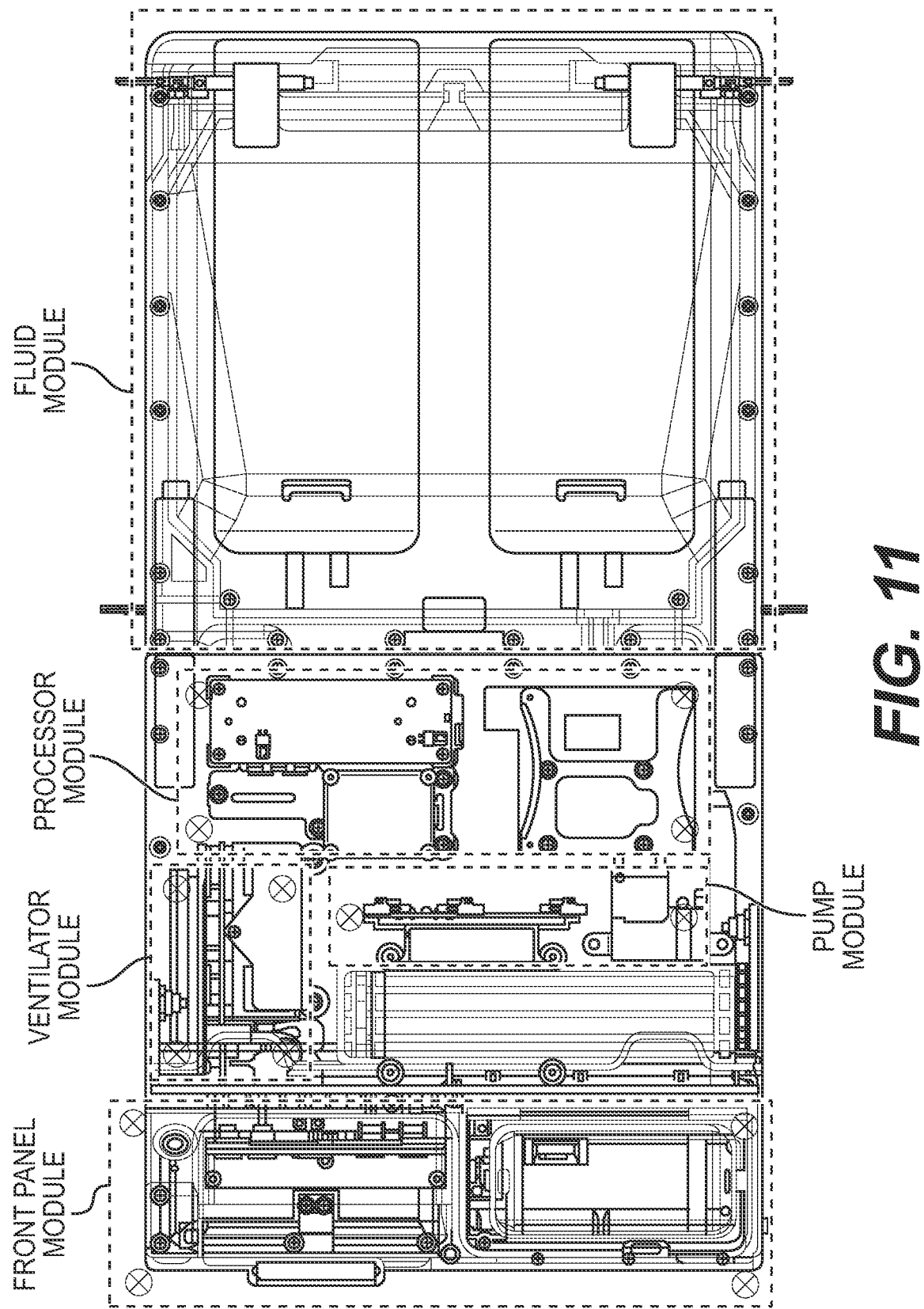

FIGS. 7-14 depict another embodiment of an ACCS 700 adapted to fit under a litter without raising the litter off the ground. Components and capabilities found in one of ACCS 100, ICCCS 400, and ACCS 700 maybe interchangeable with components and capabilities of another of ACCS 100, ICCCS 400, and ACCS 700. ACCS 700 is preferably comprised of two enclosures: front enclosure 740 and rear enclosure 745. Preferably front enclosure 740 houses the electronics, ventilator, processor, suction, pumps, control panel, battery, screen, connectors or ports, speakers, and/or other components. Rear enclosure 745 preferably houses one or more fluids for a patient. In other embodiments, rear enclosure 745 is merely structural to allow front enclosure 740 to be coupled to a litter. FIG. 11 depicts one embodiment of the components of front enclosure 740 and rear enclosure 745.

Figure 14:
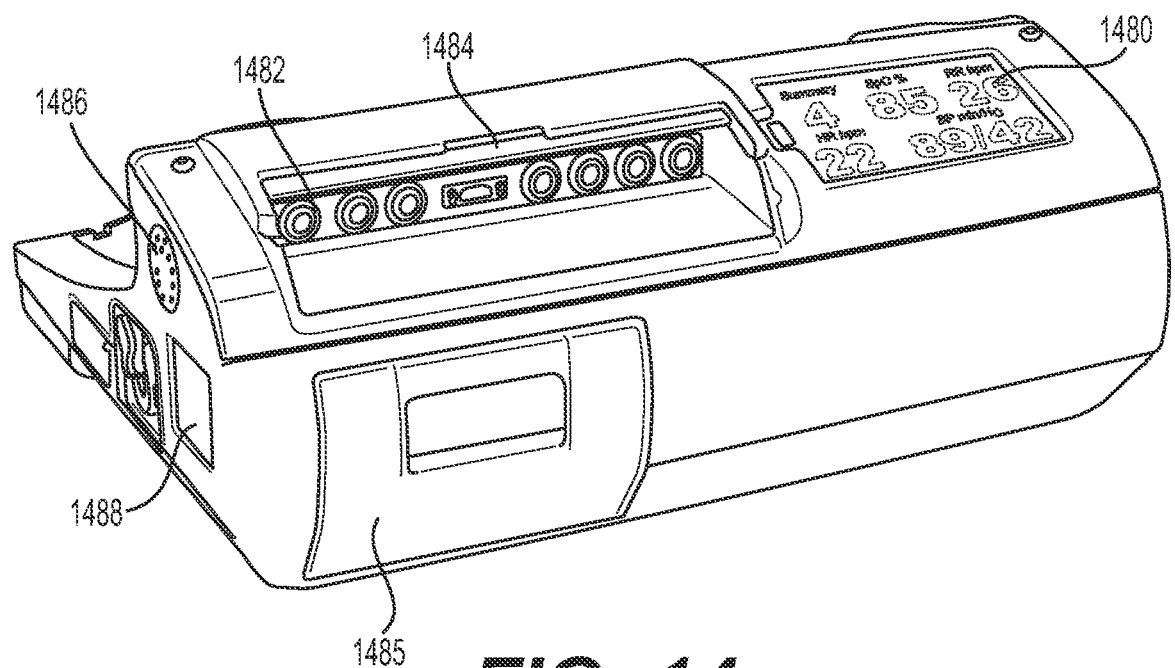

FIG. 14 depicts an embodiment of the control panel of ACCS 700. Preferably, the control panel has a screen 1480, a connector panel 1482 with a cover 1484, a storage compartment 1485, a speaker 1486, and a side display 1488. Cover 1484 preferably shields contaminants from the connection points and allows a clear site when it is needed, and contaminants are not an issue. Front enclosure 740 preferably also includes a suction reservoir module 756 (shown in FIG. 8), which may be removed and emptied or replaced, thereby isolating bodily fluids from the rest of ACCS 700.

Figure 7:
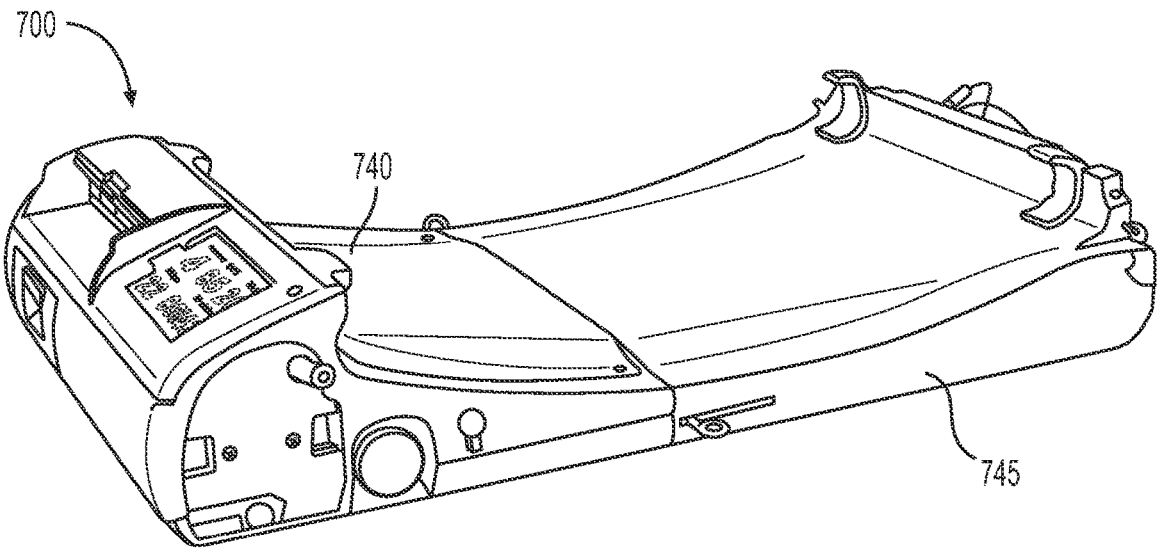
FIGS. 7-14 depict another embodiment of a system for monitoring and treating a patient.
Figure 8:
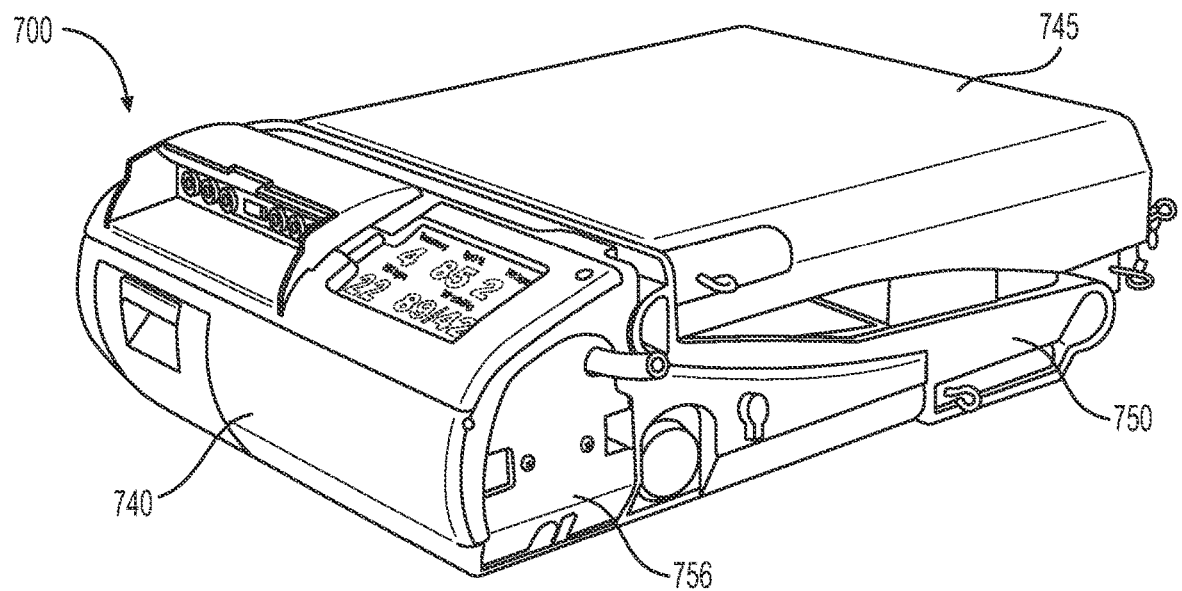

Preferably, ACCS 700 is convertible from a transportation configuration (as shown in FIG. 8) to the use configuration (as shown in FIG. 7). In the transportation configuration, a spacer 750 may be placed between the two enclosures to minimize the cross-sectional area of the shipping unit, while also carry consumables needed to deploy or use the platform. For example, FIG. 9 depicts an embodiment of spacer 750. Spacer 750 may have a storage compartment 751 to store products used in conjunction with ACCS 700. As shown in FIG. 10, one or more ACCS 700s may be able to be transported in a case 1055. Case 1055 may also transport other devices used in conjunction with the ACCS.

To assemble ACCS 700, rear enclosure 745 may be coupled to front enclosure 740. For example, front enclosure 740 may have one or more male members that are insertable into female portions of rear enclosure 745 (or vice versa). In other embodiments, front enclosure 740 and rear enclosures 745 may bolt together, clip together, slide into position, or otherwise be coupled together. Preferably once assembled, ACCS 700 has a locking mechanism that prevents the two enclosures from accidently becoming separated. Preferably, once assembled, front enclosure 740 and rear enclosure 745 are in fluid and/or data communication.

Figure 12A:
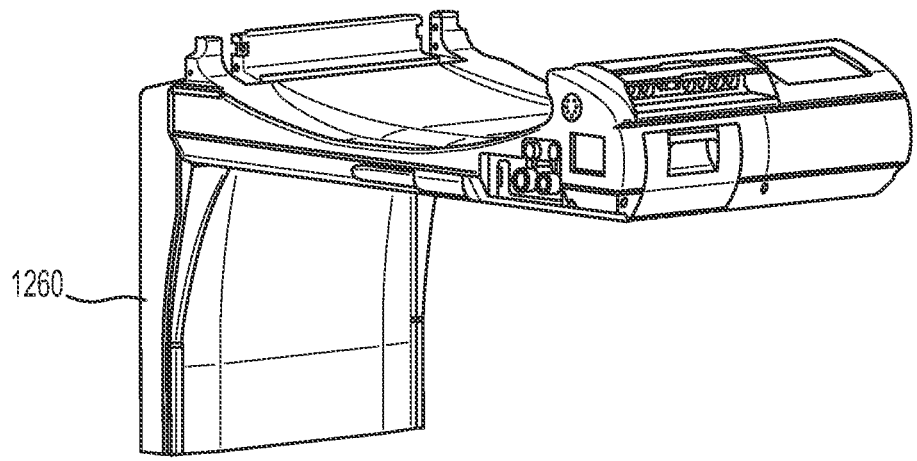
Figure 12B:
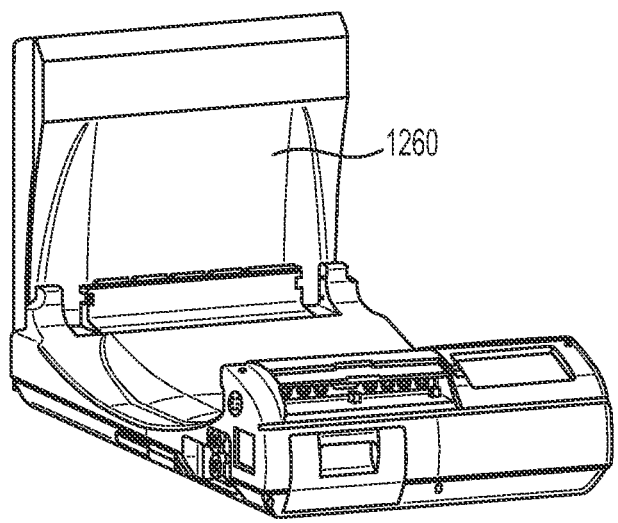

Preferably, rear enclosure 745 may have an internal fluids module. For example, as shown in FIGS. 12A and 12B, internal fluids module 1260 may be stored within rear enclosure 745 and be able to be mounted to enclosure 745 for the delivery of fluids to the patient. Fluids module 1260 preferably has a quick release and completely encloses internal routed tubing. Fluids module 1260 is preferably a consumable with the ability to be reloaded with fluid for one or more casualties.

Figure 13:
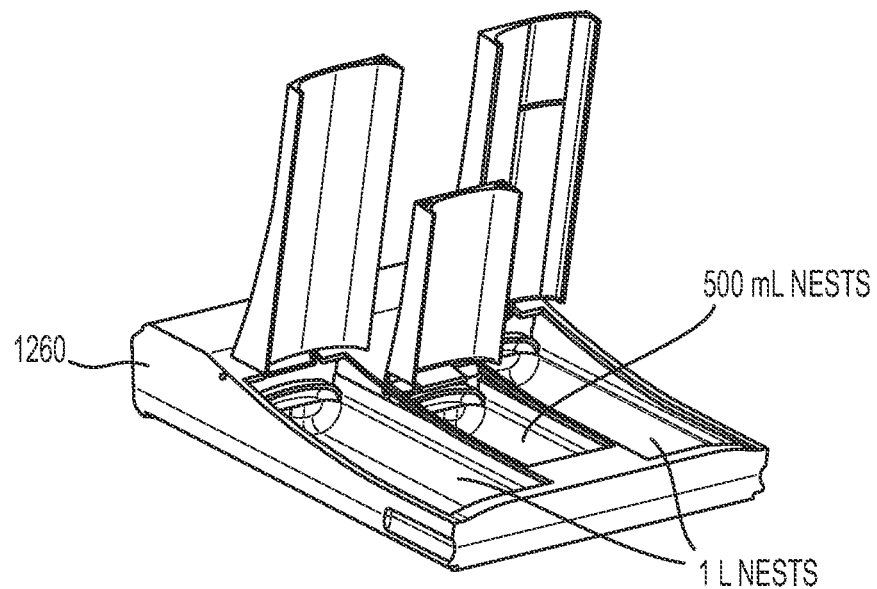

As shown in FIG. 13, fluids module 1260 may have one or more bays or nests to store fluid bags. The nests may all store the same size fluid bags or different sized fluid bags. For example, fluids module 1260 preferably has the capability to enclose two 1000 ml IV fluid bags and one 500 ml IV fluid bag, including necessary components for administration of fluids including but not limited to: a linear actuator pinch valve for controlling flow rate; an in-line flow sensor; a bubble detector; and a bubble vent solenoid. The output connections are preferably located at the back of the unit with one connection to hook up an external bag. The module preferably receives power and communication from spring pin connectors that make contact with the front enclosure.

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. It is intended that the specification and examples be considered exemplary only with the true scope and spirit of the invention indicated by the following claims. Furthermore, the term "comprising of" includes the terms "consisting of" and "consisting essentially of."

The invention claimed is:

1. A system for monitoring and treating a patient on route to a medical facility, comprising:
    a critical care unit;
    at least one patient monitoring device coupled to the critical care unit, wherein the critical care unit obtains physiological data about the patient from each patient monitoring device;
    at least one patient treatment device coupled to the critical care unit, wherein the critical care unit provides treatment instructions to each patient treatment device;
    at least one peripheral device linkage having a plurality of independent interface channels adapted to interface with one or more peripheral devices, wherein the critical care unit is adapted to automatically recognize, link to, and configure each linked peripheral device;
    a near real time two way communications device coupled to the critical care unit; and
    a remote communications terminal in communication with the two way communications device;
    wherein the critical care unit:
        determines a medical status of the patient based on dynamically changing vital state of the patient and predictive models of outcomes based on current therapy;
        divides the physiological data into packets of data;
        sends each packet of data based on the medical status to the remote communications terminal; and
        receives the treatment instructions from the remote communications terminal via the two way communications device.

2. The system of claim 1, the critical care unit further comprising a quick coupling device adapted to attach the system to a patient transport litter.

3. The system of claim 2, wherein the coupling device is adjustable to fit different sized liters or be used independent of attachment to any litter.

4. The system of claim 1, wherein at least a portion of the critical care unit is adapted to be coupled under the litter without raising the litter off the ground or changing the center of gravity of the litter-patient combination.

5. The system of claim 1, wherein the entirety of the critical care unit is adapted to be coupled under the litter.

6. The system of claim 1, wherein the critical care unit is foldable into a wearable configuration.

7. The system of claim 1, wherein the critical care unit weighs less than 30 pounds.

8. The system of claim 1, wherein the critical care unit provides at least 90% accessibility to the patient.

9. The system of claim 1, further comprising redundancies to alleviate equipment failure, to back-up the system, and to run multiple similar monitors or therapeutic devices simultaneously.

10. The system of claim 1, wherein the critical care unit is adapted to interface with at least one of medical monitors, capnography devices, multiple fluid types and IV fluid and control devices, suction devices, mechanical ventilation devices, concentrated gases, central computing platforms, and web-based user networks and interfaces.

11. The system of claim 1, wherein the at least one closed loop controlled patient treatment device is at least one of a fluid and drug therapy device, an oxygen generating device, a ventilation device, a suction device, and an analgesia/anesthesia device.

12. The system of claim 1, wherein the system is adapted to monitor and provide treatment to multiple patients simultaneously.

13. The system of claim 1, further comprising at least one visual communications device adapted to provide images of the patient to an offsite medical care giver and provide the patient with images of the offsite medical care giver.

14. The system of claim 1, wherein the packets of data are transmitted at different time intervals.

15. The system of claim 1, wherein the critical care unit sends near real time updates to the physiological and treatment/therapy data.

16. The system of claim 15, wherein the updates are sent at one of regular intervals, upon demand, or as the physiological data of the patient changes.

17. A portable critical care unit adapted to monitor and treat a patient on route to a medical facility, comprising:
    at least one patient monitoring device, wherein the critical care unit obtains physiological data about the patient from each patient monitoring device;
    at least one patient treatment device, wherein the critical care unit provides treatment instructions to each patient treatment device; a two way communications device adapted to send physiological data and receive treatment instructions;
    at least one peripheral device linkage having a plurality of independent interface channels adapted to interface with one or more peripheral devices, wherein the critical care unit is adapted to automatically recognize, link to, and configure each linked peripheral device; and
    a coupling device adapted to attach the critical care unit to a patient transport litter;
    wherein the critical care unit:
        determines a medical status of the patient based on dynamically changing vital state of the patient and predictive models of outcomes based on current therapy;
        divides the physiological data into packets of data;
        sends each packet of data based on the medical status to the remote communications terminal; and
        receives the treatment instructions from the remote communications terminal via the two way communications device.

18. The critical care unit of claim 17, wherein the coupling device is adjustable to fit different sized liters or be used independent of attachment to any litter.

19. The critical care unit of claim 17, wherein at least a portion of the critical care unit is adapted to be coupled under the litter without raising the litter off the ground or changing the center of gravity of the litter-patient combination.

20. The critical care unit of claim 17, wherein the entirety of the critical care unit is adapted to be coupled under the litter.

21. The critical care unit of claim 17, wherein the critical care unit is foldable into a wearable configuration.

22. The critical care unit of claim 17, wherein the critical care unit weighs less than 30 pounds.

23. The critical care unit of claim 17, wherein critical care unit provides at least 80% accessibility to the patient.

24. The critical care unit of claim 17, further comprising redundancies to alleviate equipment failure, to back-up the system, and to run multiple similar monitors or therapeutic devices simultaneously.

25. The critical care unit of claim 17, wherein the critical care unit is adapted to interface with at least one of medical monitors, capnography devices, multiple fluid types and IV fluid and control devices, suction devices, mechanical ventilation devices, concentrated gases, central computing platforms, and web-based user networks and interfaces.

26. The critical care unit of claim 17, wherein the at least one closed loop controlled patient treatment device is at least one of a fluid and drug therapy device, an oxygen generating device, a ventilation device, a suction device, and an analgesia/anesthesia device.

27. The critical care unit of claim 17, wherein the critical care unit is adapted to monitor and provide treatment to multiple patients simultaneously.

28. The critical care unit of claim 17, further comprising at least one visual communications device adapted to provide images of a patient to an offsite medical care giver and provide the patient with images of the offsite medical care giver.

29. The care unit of claim 17, wherein the packets of data are transmitted at different time intervals.

30. The care unit of claim 17, wherein the critical care unit sends updates to the physiological data.

31. The care unit of claim 30, wherein the updates are sent at one of regular intervals, upon demand, or as the physiological data of the patient changes.

* * * * *